US012623041B2

(12) United States Patent
Namon

(10) Patent No.: US 12,623,041 B2
(45) Date of Patent: May 12, 2026

(54) AIRFLOW NASAL PRONG

(71) Applicant: Ari Namon, Lakeville, CT (US)

(72) Inventor: Ari Namon, Lakeville, CT (US)

( * ) Notice: Subject to any disclaimer, the term of this patent is extended or adjusted under 35 U.S.C. 154(b) by 821 days.

(21) Appl. No.: 17/839,874

(22) Filed: Jun. 14, 2022

(65) Prior Publication Data

US 2022/0401683 A1 Dec. 22, 2022

Related U.S. Application Data

(60) Provisional application No. 63/210,245, filed on Jun. 14, 2021.

(51) Int. Cl.
*A61M 16/06* (2006.01)
*A61M 16/08* (2006.01)

(52) U.S. Cl.
CPC .... *A61M 16/0666* (2013.01); *A61M 16/0816* (2013.01); *A61M 16/0672* (2014.02)

(58) Field of Classification Search
CPC ........ A61B 17/12045; A61B 17/12104; A61B 17/12136; A61B 17/24; A61B 2017/12127; A61F 13/36; A61F 5/08; A61J 15/0003; A61K 9/0043; A61M 15/002; A61M 15/0028; A61M 15/0045; A61M 15/08; A61M 15/085; A61M 16/0461; A61M 16/0488; A61M 16/06; A61M 16/0666; A61M 16/0672; A61M 16/0683; A61M 16/0688; A61M 16/101; A61M 16/108; A61M 16/16; A61M 2025/0226; A61M 2025/0266; A61M 2202/0007;

(Continued)

(56) References Cited

U.S. PATENT DOCUMENTS 658,436 A * 9/1900 Groth ................... A61M 15/08
128/203.18
2,335,936 A * 12/1943 Hanlon .................... A61F 5/08
128/207.18

(Continued)

FOREIGN PATENT DOCUMENTS

EP 1957170 B1 1/2017
WO 2015041547 A1 3/2015
WO 2016159787 A1 6/2016

OTHER PUBLICATIONS

International Search Report for Corresponding Application Serial No. PCT/US2022/033377, Dated Oct. 5, 2022.

(Continued)

*Primary Examiner* — Annette Dixon
(74) *Attorney, Agent, or Firm* — Tarolli, Sundheim, Covell & Tummino LLP

(57) ABSTRACT

A nasal prong comprising a tube configured to be partially placed in a nasal passage of a patient, the tube having a first end, a second end, and an intermediate portion, and a lumen extending therebetween. The first end having an elongated opening configured to face supero-medially within the nasal passage, wherein airflow out of the elongated opening is directed superiorly and posteriorly within the nasal cavity, above the inferior concha, around the middle concha, and towards the roof of the nose. The intermediate portion of the tube having a bend that keeps the nasal prong on a floor of the nasal passage at and/or near the outer edge of a nostril.

20 Claims, 7 Drawing Sheets

(58) Field of Classification Search

CPC .... A61M 2202/0208; A61M 2202/025; A61M 2202/03; A61M 2205/0266; A61M 2205/32; A61M 2205/3337; A61M 2205/6081; A61M 2209/088; A61M 2210/0618; A61M 2230/005; A61M 25/0023; A61M 25/02; A61M 31/00; A61M 31/002

See application file for complete search history.

(56) References Cited

U.S. PATENT DOCUMENTS

| | | | | |
|---|---|---|---|---|
| 3,568,678 A * | 3/1971 | Pourquier | ............. | A61M 31/00 |
| | | | | 128/207.18 |
| 3,643,660 A * | 2/1972 | Hudson | ............. | A61M 16/0672 |
| | | | | 128/207.18 |
| 3,867,946 A * | 2/1975 | Huddy | ............. | A61M 16/0666 |
| | | | | 128/207.18 |
| 3,903,893 A * | 9/1975 | Scheer | ............. | A61B 17/12136 |
| | | | | 604/101.05 |
| 4,821,715 A * | 4/1989 | Downing | .......... | A61M 16/0461 |
| | | | | 128/207.18 |
| 5,601,594 A * | 2/1997 | Best | .......................... | A61F 5/08 |
| | | | | 606/199 |
| 5,797,392 A * | 8/1998 | Keldmann | ........ | A61M 15/0028 |
| | | | | 128/203.23 |
| 6,626,179 B1 * | 9/2003 | Pedley | ...................... | A61F 2/18 |
| | | | | 128/207.18 |
| 7,856,979 B2 * | 12/2010 | Doshi | .................... | A62B 23/06 |
| | | | | 128/850 |
| 8,056,562 B2 * | 11/2011 | Sherman | ........... | A61M 16/0488 |
| | | | | 128/207.18 |
| 8,092,478 B2 * | 1/2012 | Kotler | ............... | A61M 16/0666 |
| | | | | 606/191 |
| 8,997,747 B2 * | 4/2015 | Hobson | ............. | A61M 16/0672 |
| | | | | 128/207.18 |
| 9,943,660 B2 | 4/2018 | Selvarajan et al. | | |
| 2005/0121038 A1 * | 6/2005 | Christopher | ...... | A61M 16/0666 |
| | | | | 128/207.14 |
| 2015/0165151 A1 * | 6/2015 | Payton | ............. | A61M 16/0688 |
| | | | | 128/205.25 |
| 2016/0022077 A1 | 1/2016 | Rakhamimov et al. | | |
| 2016/0220775 A1 * | 8/2016 | Gulliver | ........... | A61M 16/0672 |
| 2019/0314588 A1 * | 10/2019 | Beck | ................... | A61M 31/002 |
| 2020/0000896 A1 | 1/2020 | Robitaille | | |
| 2020/0405991 A1 | 12/2020 | Leonard et al. | | |

OTHER PUBLICATIONS

Extended European search report dated May 9, 2024 for corresponding Application No./Patent No. 22825643.4-1122/4355399 PCT/US2022033377, 7 pages.

* cited by examiner

60

PLACE A NASAL PRONG PARTIALLY WITHIN A NASAL PASSAGE
OF A PATIENT

62

ALIGN THE NASAL PRONG IN THE NASAL PASSAGE SO THE
BEND OF THE INTERMEDIATE PORTION IS ON THE FLOOR OF
THE NASAL PASSAGE

64

DISPENSE A MIXTURE OF OXYGEN THROUGH THE NASAL
PRONG TOWARDS THE TOP OF THE NASAL PASSAGE AND
THE NASAL CONCHAE

66

AIRFLOW NASAL PRONG

CLAIM OF PRIORITY

This application claims priority to U.S. Provisional Application Ser. No. 63/210,245, filed Jun. 14, 2021, entitled "IMPROVED AIRFLOW NASAL CANNULA". The entirety of this provisional application is hereby incorporated by reference for all purposes.

TECHNICAL FIELD

The present disclosure relates generally to a nasal prong for a nasal cannula and, more specifically, to a nasal prong shaped to improve airflow through the nasal passage.

BACKGROUND

Nasal cannulas, which can include nasal prongs, are used to deliver supplemental oxygen to patients who require it for both short- and long-term use. Standard low-flow nasal cannulas deliver oxygen via small prongs inserted into the nostrils at flow rates of 2 to 6 liters per minute. The traditional method of gas delivery through cannula prongs is non-physiologic because the gas bypasses the nasal valve, an area just inside the nostril which creates turbulent flow resulting in distribution of the gas over the complex redundant anatomy of the nasal cavity, of which conchae play a critical role. The conchae act as aerodynamic baffles increasing surface area and distributing the gas over a larger mucosal surface for exchange of heat and moisture, and to filter the gas.

The nasal cavity serves three functions: it warms, humidifies, and filters inspired gases. All three functions are diminished or altogether bypassed by the standard prong design. Traditional cannula prong design results in primarily laminar flow along the floor of the nose, which bypasses the conchae and causes crusting, dryness, nosebleeds, septal perforation, discomfort, air hunger, and possibly reduced alveolar gas exchange. These complications ultimately result in poor patient compliance.

SUMMARY

The present disclosure relates generally to a nasal prong for a nasal cannula and, more specifically, to a nasal prong shaped to improve airflow through the nasal passage.

A nasal prong that can improve airflow into the airway of a patient. The nasal prong comprising a tube configured to be partially placed in a nasal passage of a patient, the tube having a first end, a second end, and an intermediate portion, and a lumen extending therebetween. The first end having an elongated opening configured to face supero-medially within the nasal passage, wherein airflow out of the elongated opening is directed superiorly and posteriorly within the nasal cavity, above the inferior concha, around the middle concha, and towards the roof of the nose of the patient. The intermediate portion of the tube having a bend that keeps a portion of the nasal prong on a floor of the nasal passage at and/or near the outer edge of a nostril.

A method for using a nasal prong to improve airflow into the airway of a patient comprising the following steps. Placing a nasal prong partially within a nasal passage of a patient, wherein the nasal prong is part of a nasal cannula and the nasal prong comprises: a tube configured to be partially placed in a nasal passage of a patient, the tube having a first end, a second end, and an intermediate portion, and a lumen extending therebetween, the first end having an elongated opening configured to face superiorly within the nasal passage, and the intermediate portion of the tube having a bend that keeps the nasal prong on a floor of the nasal passage. aligning the nasal prong in the nasal passage of the patient so the bend of the intermediate portion is on the floor of the nasal passage. Dispensing a mixture of oxygen through the nasal prong, wherein the mixture of oxygen flows out of the elongated opening of the nasal prong towards the top of the nasal passage and the nasal conchae.

A nasal prong that can improve airflow into the airway of a patient. The nasal prong can comprise a tube configured to be partially placed in a nasal passage of a patient, the tube having a first end, a second end, and an intermediate portion, and a lumen extending therebetween. The second end can comprise an opening that can receive laminar airflow. A portion of the lumen can be configured to alter the laminar airflow to turbulent airflow. The first end can be configured to be positioned within the nasal passage and comprises another opening configured to direct the turbulent airflow into the nasal passage in a physiological manner.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 6A-7B show computer generated models of airflow through a nasal cavity with a traditional nasal prong (FIGS. 6A and 7A) compared to airflow through a nasal cavity with a modified nasal prong of FIG. 1 or 4.

DETAILED DESCRIPTION

I. Definitions

Figure 1:
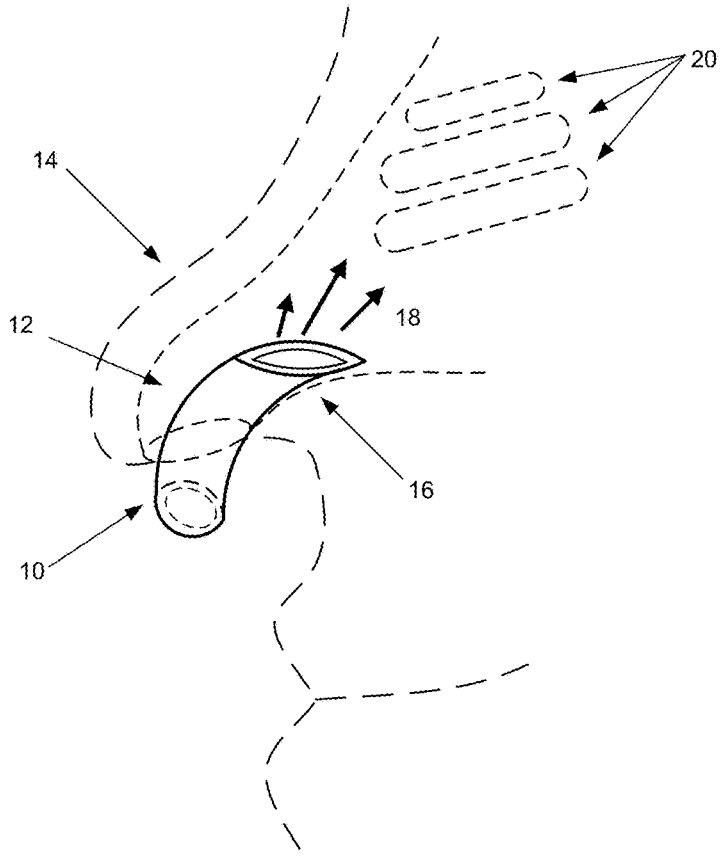
FIG. 1 is a side view of an exemplary nasal prong with a bend within the nose of a patient.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise. As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to a nasal prong for a nasal cannula that improves airflow through the nasal passage. The improved nasal prong solves the problems of traditional nasal cannula and nasal prongs by modifying the cannula tip (prong) to more closely represent the functions of the nasal valve. The improved nasal prong can include a myriad of modifications to the cannula prongs, including baffles, ridges, crimps, rifling, and bending to both redirect flow and create turbulence. By producing turbulent flow directed superiorly over the inferior concha and around the middle concha, natural airflow dynamics will be reproduced and thus more closely resemble normal nasal physiology. By directing the flow superiorly, the receptors that detect airflow and relieve air hunger will be stimulated, whereas the receptors are not stimulated with traditional nasal prong and/or cannula designs. Most patients who use nasal cannulas chronically suffer from chronic obstructive pulmonary disease (COPD) and already experience air hunger. Traditional nasal prongs and/or cannulas worsen a COPD patient's feeling of air hunger even while delivering oxygen. Additionally, the gas will be better conditioned by the nasal mucosa, raising its temperature and humidity level to reduce crusting, dryness, nosebleed, perforation risks, and patient discomfort. Improved nasal prongs that direct airflow in a more natural direction may also improve alveolar gas exchange because optimal exchange requires the gas to be at 100% humidity and normal body temperature. The closer to physiological parameters the inspired gas, the better prepared it is for introduction to the lungs.

III. Systems

An aspect of the present disclosure is a nasal prong 10 (FIG. 1) designed to improve airflow through the nasal passage 12 of a patient 14 needing a nasal cannula (e.g., a COPD patient). The nasal prong 10 is positioned within the nasal passage 12 such that a bend in the nasal prong can rest against a portion of the nasal floor 16 at and/or near an outer edge of the nostril (not labeled) and airflow 18 out of the nasal prong is directed superiorly and posteriorly within the nasal cavity, above the inferior concha, around the middle concha, and towards a roof or vault of the nose. The inferior concha, the middle concha, and the superior concha make up the nasal conchae 20. Airflow 18 can be a mixture of oxygen from, for example, an oxygenator or oxygen concentrator connected to the nasal prong 10 via tubing (e.g., medical grade plastic tubing). The airflow 18 that exits out of the nasal prong 10 into the nasal passage 12 can be non-laminar (e.g., turbulent). The nasal prong 10 can be configured to increase at least one of humidity and temperature of the airflow 18 before the airflow reaches alveoli (not shown) of the patient. Directing the non-laminar (e.g., turbulent) airflow towards the nasal conchae 20 can increase evaporative heat exchange between the air and mucosa (not shown) as compared to airflow from a traditional nasal prong, which increases at least one of the humidity and temperature of the airflow before it reaches the alveoli. Additionally, by directing the flow superiorly, receptors in the nasal passages that detect airflow and relieve air hunger will be stimulated. The nasal prong 10 can be a continuous part of a nasal cannula (not shown) or it can be an attachable addition to a nasal cannula (not shown) for directing a supplementary oxygen mixture to the patient. The configuration and positioning of the nasal prong 10 can increase the oxygen saturation of the patient compared to a traditional nasal prong.

Figure 2:
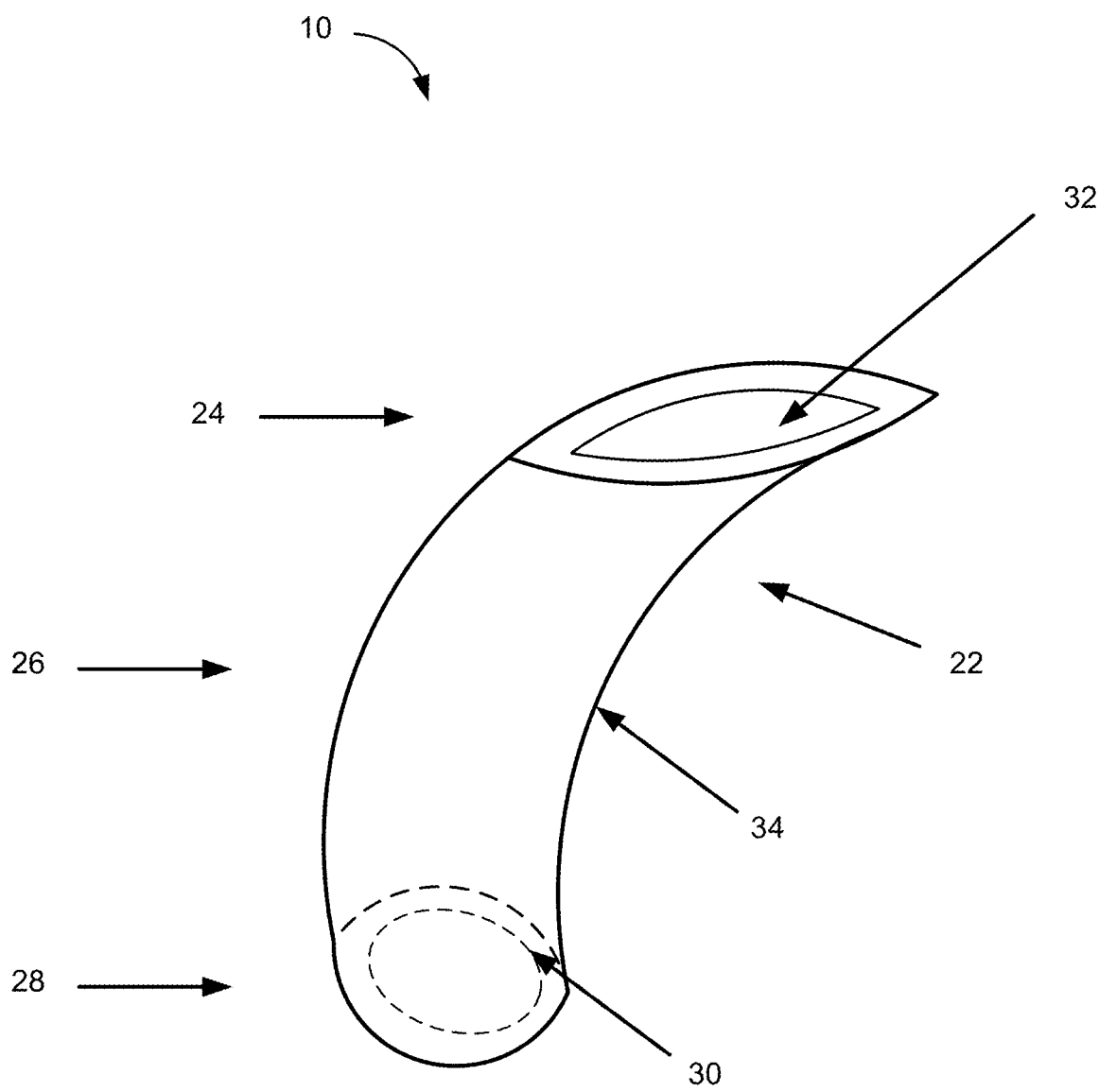
FIG. 2 is a schematic diagram of a nasal prong with a bend.

FIG. 2 shows the nasal prong 10 in greater detail. The nasal prong comprises a tube 22 having a first end 24, an intermediate portion 26, and a second end 28. The tube 22 also includes a lumen 30 extending from the first end to the second end for fluid communication between openings in the first end and the second. The tube 22 is configured to be partially placed in a nasal passage of a patient. For example, the tube 22 can be placed in the nasal passage 12 as shown in FIG. 1. The tube 22 can also be placed in the nasal passage in any other configuration comfortable for the patient and directing airflow superiorly and posteriorly within the nasal cavity, above the inferior concha, around the middle concha, and towards the roof or vault of the nose (e.g., to any depth as long as the first end is within the nasal passage and the second end is outside the nasal passage). The tube 22 can be positioned such that the first end 24 can be positioned within the nose but near a portion of an outer nasal wall of the patient. The tube can be of a length that stays in place in the nasal opening easily, without the use of additional attachment components, and does not further obstruct and/or negatively effect the airflow (e.g., so the airflow stays with the majority of airflow traveling through the middle third of the nasal cavity, around the middle turbinate, about 15% traveling in the lower third, and about 15% traveling in the upper third.

The first end 24 of the nasal prong 10 has an elongated opening 32 configured to face supero-medially within the nasal passage so that airflow that flows out of the elongated opening is directed superiorly and posteriorly within the nasal cavity, above the inferior concha, around the middle concha, and towards the roof or vault of the nose (as shown in FIG. 1). For example, the angle of the airflow can be between 30 and 60 degrees superior from the floor of the nasal passage. In another example, the angle of airflow can be approximately 45 degrees. The elongated opening 32 can be ovular or elliptical in shape. The first end 24 can be cut at an angle relative to the second end 28, such that the elongated opening 32 directs airflow so that the majority of airflow travels through the middle third of the nasal cavity, around the middle turbinate, about 15% travels in the lower third of the nasal cavity, and about 15% travels in the upper third of the nasal cavity. The angle of the first end 24 compared to the second end 28 can be, for example, 15°, 30°, 40°, 45°, 50°, 60°, or the like. The angle can correct the airflow from the nasal prong such that it protects the tissue underneath from the oxygen flow and directs the oxygen flow into the inhaled air stream restoring the normal airflow path The intermediate portion 26 of the tube 22 has a bend 34 that keeps the nasal prong 10 on the floor of the nasal passage at and/or near the outer edge of a nostril. The angle of the bend 34 of the intermediate portion 26 of the tube 22 (and the outer size of the tube) can also keep a portion of the nasal prong in contact with the outer nasal wall. The second end 28 of the nasal prong 10 can be configured to attach to a pre-existing nasal cannula or can be configured as part of a nasal cannula. The second end 28 of the nasal prong can be in fluid communication with an oxygen device (e.g., oxygenator, oxygen concentrator, etc.) so that a mixture of oxygen can flow through the lumen 30 and out the elongated opening 32 into the nasal passage of the patient to deliver oxygen to the lungs of the patient.

The elongated opening 32 of the nasal prong 10 can be positioned to direct airflow superiorly and posteriorly within the nasal cavity, above the inferior concha, around the middle concha, and towards the roof or valve of the nose in a manner similar to the physiologic flow of air through a non-obstructed nasal passage without diverting the flow from the middle turbinate. For example, the angle of the airflow can be between 30 and 60 degrees superior of the nasal floor, such as approximately 45 degrees. Directing air up over the inferior concha and around the middle concha allows air to be humidified by the conchae and to reach a temperature closer to normal body temperature. Directing airflow in this way reduces at least one of an oxygen hunger, a nasal dryness, a nosebleed risk, a perforation risk, a discomfort, and a mucous crusting of the patient. Creating turbulence in the airflow can also improve patient inspiration, and comfort during inspiration. Not shown, the interior of the lumen 30 can also include at least one of baffles, ridges, crimps, or rifling that disrupt the laminar flow of the air through the lumen. The number, size, and location of the baffles, ridges, crimps, or rifling can cause different turbulence in the airflow. The addition of turbulence to the airflow can more correctly mimic traditional inspiration of air through a nose of a person without a breathing problem.

The nasal prong 10 can be constructed from any suitable flexible material, such as the medical grade plastic tubing used in traditional cannulas. The material can be biocompatible. The nasal prongs can be created using traditional techniques such as injection molding (e.g., using an aluminum mold), 3-D printing, dip molding, or by modifying existing nasal prongs (e.g., cutting off a tip of the existing nasal prong at an angle).

Figures 3A, 3B, 3C:
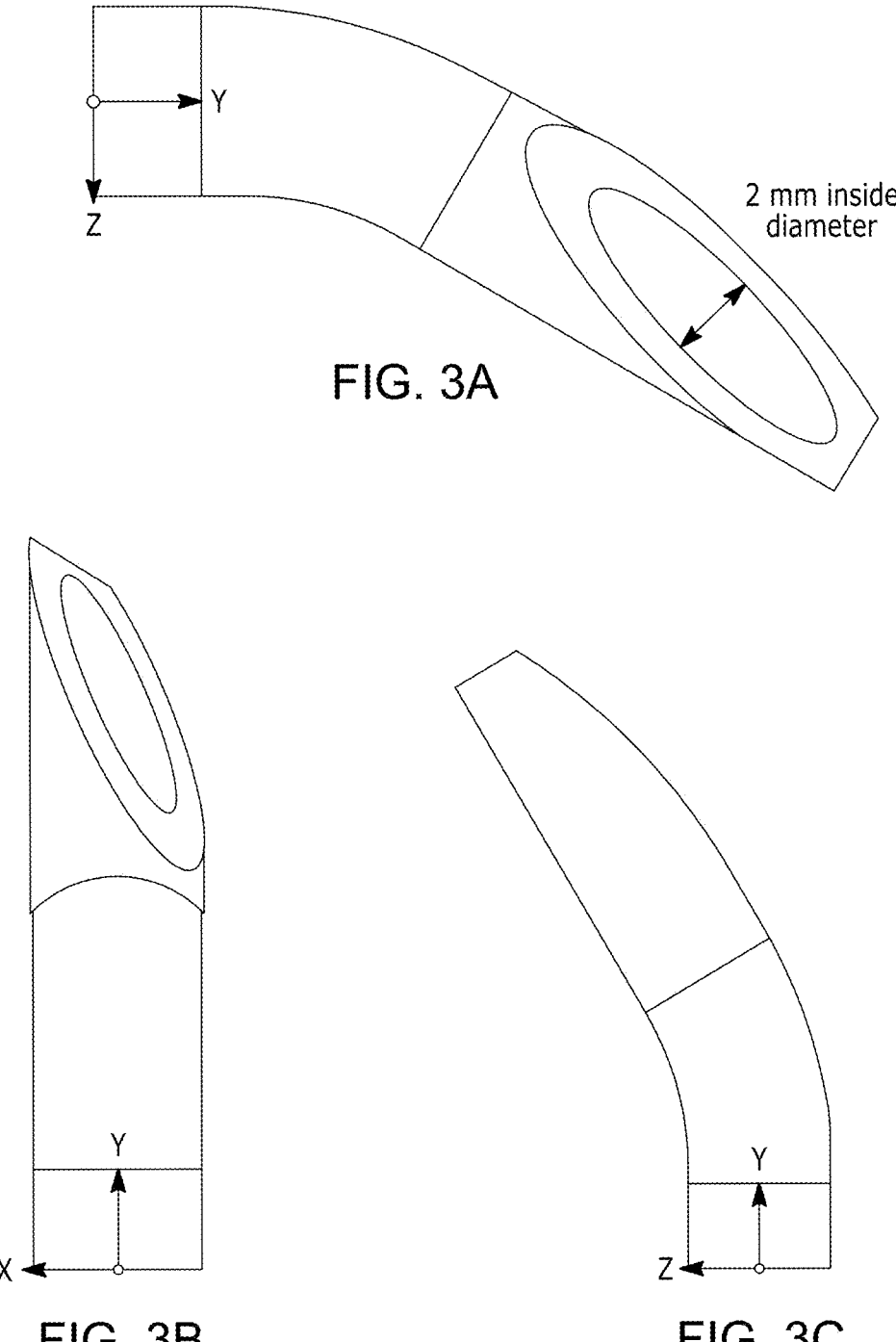
FIGS. 3A-3C are models of the nasal prong of FIG. 2 shown from different viewpoints.

FIGS. 3A-3C show views of a model of the nasal cannula from different angles. FIG. 3A is a sideways side view (along the x-axis) of the intermediate portion and the first end of the nasal prong. The model illustrates the angle of the bend of the intermediate portion, which can be between 0° and 90°, or 0° and approximately 45°, from the y-axis. The model also shows the minor axis diameter of the elongated opening of the first end can be approximately 2 mm in diameter. For example, the elongated opening can have a minor axis diameter of 2 mm and a major axis diameter of greater than 2 mm. FIG. 3B is a forward side view (along the z-axis) of the intermediate portion and the first end of the nasal prong. The model illustrates the angle of the cut on first end that creates the elongated opening. The angle can be, for example between 0° and −90°, or 0° and −45°, from the y-axis. FIG. 3C shows another view of the intermediate portion and the first end of the nasal prong along the x-axis. The model shows the angle of the bend in the intermediate portion of the nasal prong between the y-axis and the z-axis can be between 0° and −90°, or 0° and −45°, from the y-axis. The diameter(s) of the elongated opening and the degree of bend of the intermediate portion of the nasal prong can be proportioned for a specific patient, based on personal measurements or proportioned for patients with anatomy measuring within a certain percentile range (e.g., 30%-70%, 10%-35%, etc.). The shapes of the openings are shown in the models as elliptical, but can be any shape (e.g., rectangular, triangular, polygonal, etc.).

Figure 4:
FIG. 4 is another view of an exemplary nasal prong that can output turbulent flow.
Figure 4:
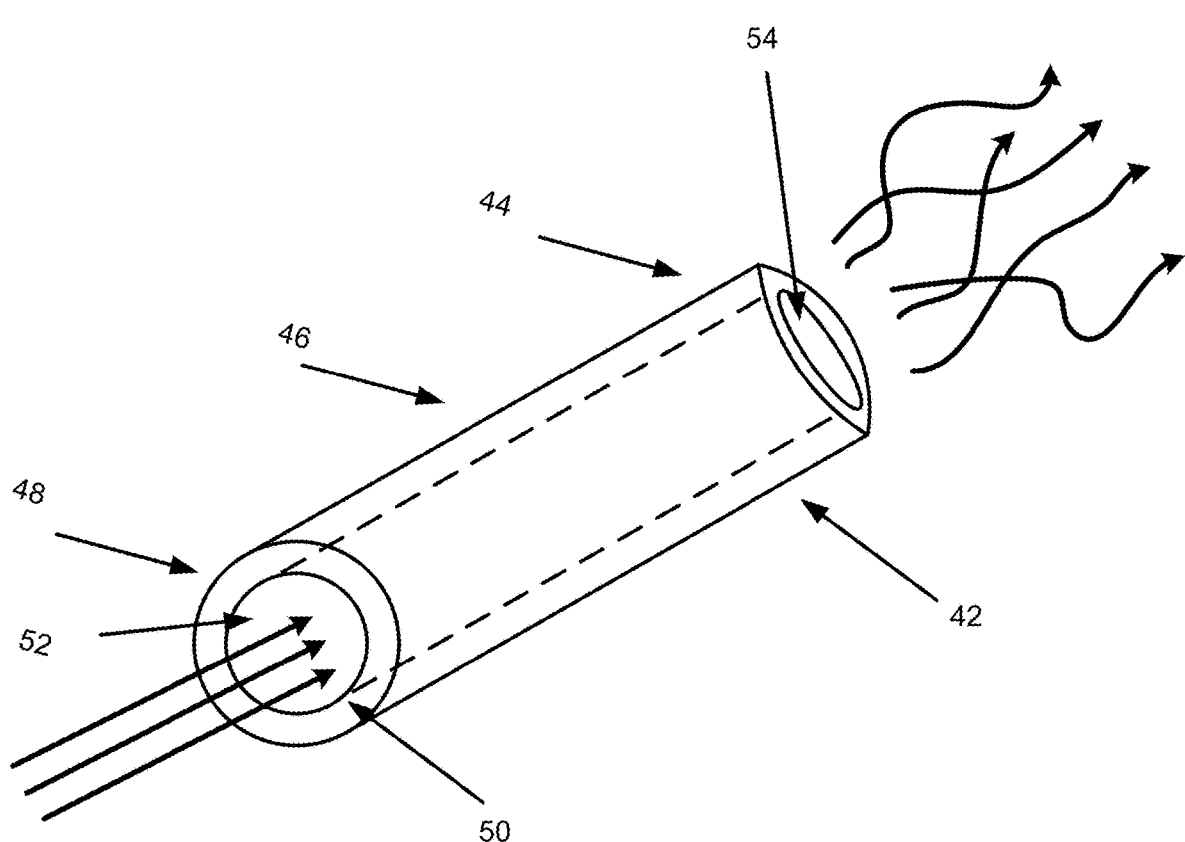

FIG. 4 shows a nasal prong 40 that can direct turbulent airflow into the nasal passage of a person wearing the nasal prong in a manner that accurately reflects physiological nasal airflow. The nasal prong 40 is a tube 42 that can be partially placed in a nasal passage of a patient. The tube 42 can have a first end 44, a second end 48, and an intermediate portion 46, and a lumen 50 extending therebetween. The second end 48 can include an opening 52 that can receive laminar airflow (represented as straight arrows). The second end 48 can connect to a nasal cannula (not shown) in fluid communication with an oxygen source (not shown), and the oxygen source can direct laminar airflow through the nasal cannula and into the opening 52. A portion of the lumen 50 can be configured to alter the laminar airflow to turbulent airflow (represented as curved arrows). The portion of the lumen 50 is an interior of the lumen that can include at least one of baffles, ridges, crimps, and rifling to redirect and add turbulence to the laminar airflow to create the turbulent airflow (see FIGS. 5A-5D). The first end 44 of the tube 42 can be positioned within the nasal passage (not shown) and can include another opening 54 that can direct the turbulent airflow into the nasal passage. The first end can be shaped to closely follow the contours of the floor of the outer edge of the opening to the nasal cavity. The opening 52 and the another opening 54 are shown as circles but can be any shape, such as, an oval, a polygon, a rectangle, or the like. The opening 52 and the other opening 54 can be different shapes. The intermediate portion 46 can also include a bend (such as shown in nasal prong 10 of FIGS. 1 and 2) such that the other opening 54 of the first end 44 is configured to direct the turbulent airflow at least partially superiorly within the nasal passage. The first end 44 can be cut at an angle relative to the second end 48, such that the other opening 54 directs airflow so that the majority of airflow travels through the middle third of the nasal cavity, around the middle turbinate, about 15% travels in the lower third of the nasal cavity, and about 15% travels in the upper third of the nasal cavity. The angle of the first end 44 compared to the second end 48 can be, for example, 15°, 30°, 40°, 45°, 50°, 60°, or the like. The angle can correct the airflow from the nasal prong such that it protects the tissue underneath from the oxygen flow and directs the oxygen flow into the inhaled air stream restoring the normal airflow path.

Figures 5A, 5B, 5C, 5D:
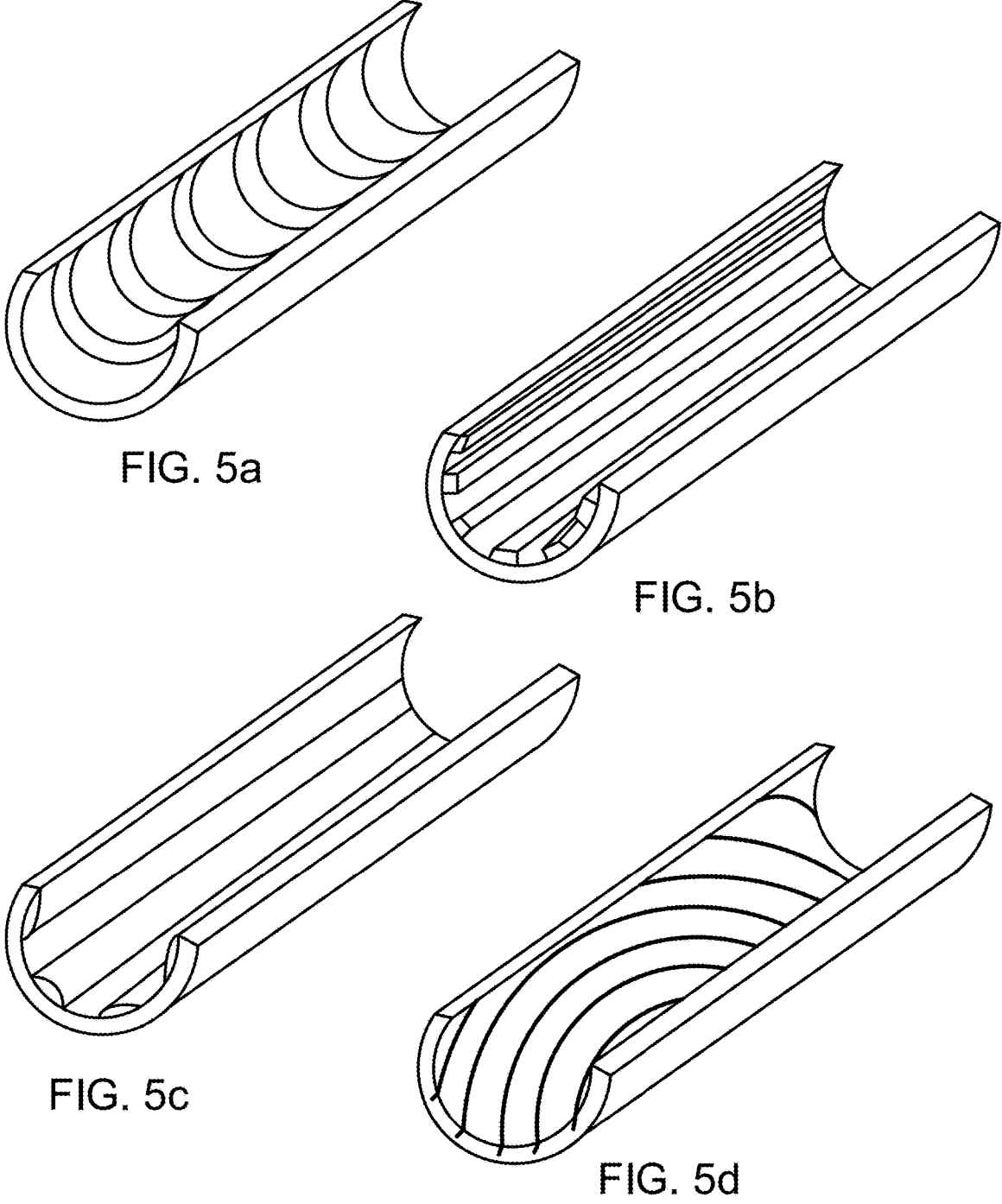
FIGS. 5A-5D show cut views of the nasal prong of FIG. 4 with different modifications to the lumen.

FIGS. 5A-5B show cut views of the nasal prong shown in FIG. 4 such that the lumen is visible. A portion of the lumen can include at least one of baffles, ridges, crimps, and rifling to redirect and add turbulence to create the turbulent airflow sent into the patient's nasal passage. FIG. 5A shows one example of baffling, that is one or more surfaces placed inside of an area (the tube) to inhibit direct motion from one part to another without preventing motion altogether. One configuration of baffling is shown, but any other configuration of baffling is contemplated and can replace the shown example. The baffling can, for example, cause whistling in the airflow FIG. 5B shows one example of the lumen including ridges. The ridges are shown as narrow, raised, rectangular bands parallel to the direction of the airflow, but can be in any direction (e.g., perpendicular, on an angle, or the like), size, or shape that can change laminar airflow to turbulent airflow. FIG. 5C shows an example of the lumen including one example of crimps that are any type of a curled, waved, or folded, compressed edge on the interior of the lumen. Other types of crimps, for example, include trapezoidal crimps, trapezoidal indent crimps, square crimps, hexagonal crimps, or the like. FIG. 5D shows an example of rifling on the lumen, where the rifling is an arrangement of spiral grooves on the lumen of the tube. The rifling can have angle of spiral, depth of groove, and/or width of groove to create turbulent airflow. The rifling can, for example, create a vortex in the airflow.

Figures 6A, 6B:
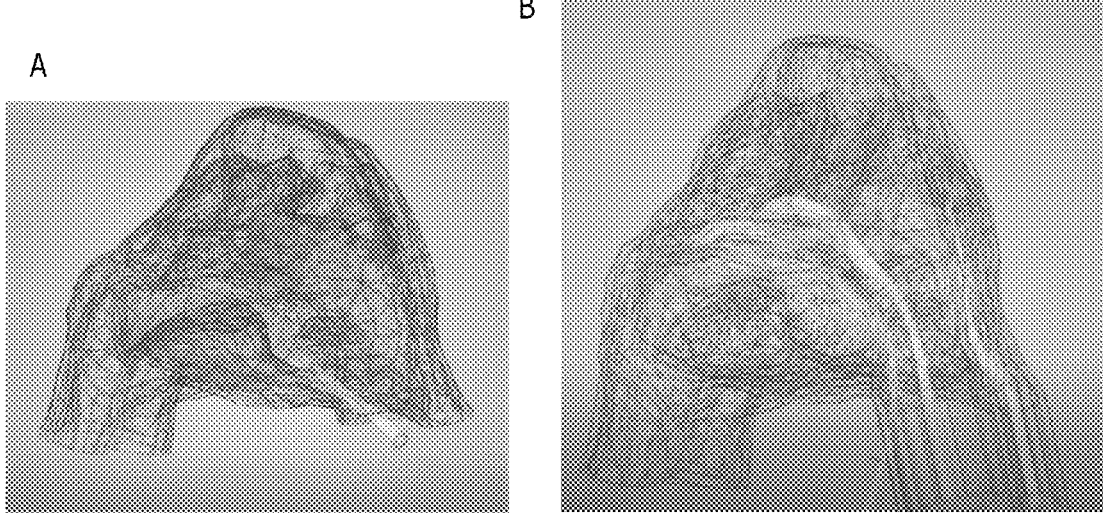
Figures 7A, 7B:
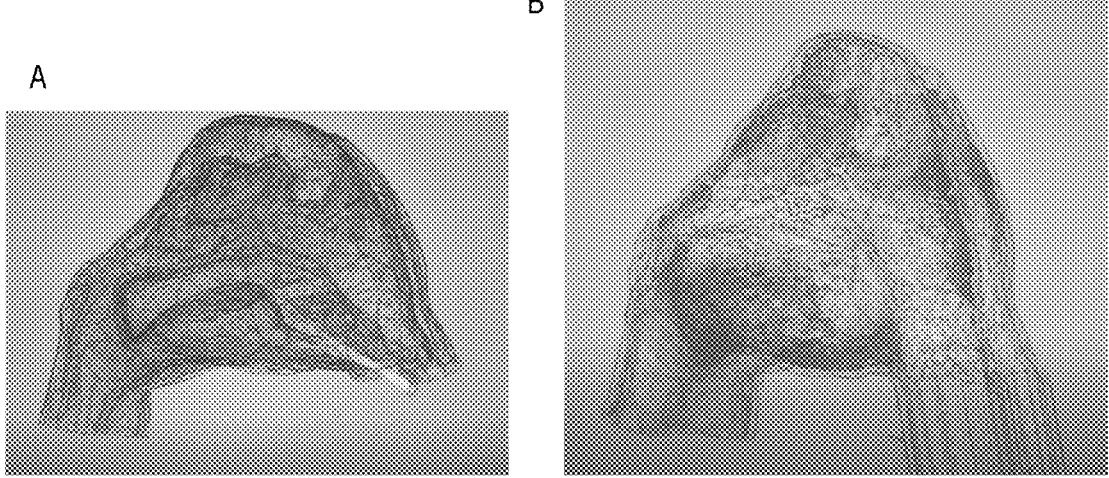

FIGS. 6 and 7 show computer generated models of the nasal cavity of a person and the airflow through a traditional nasal prong and a nasal prong as described herein. Placement of a traditional nasal prong significantly obstructs the nasal cavity and changes normal physiological airflow inside the nasal cavity. FIG. 6, element A and FIG. 7, element A show the laminar airflow that is delivered to the nasal passage via a traditional nasal prong. As shown the laminar airflow is directed to only lower portions of the nasal passage. A traditional nasal prong obstructs the airflow in the nasal opening. Computational modeling (see FIG. 6, element A and FIG. 7, element A) shows that the obstruction based on traditional nasal prong designs redirects a majority of the airflow to the underside of the middle turbinate especially when the cannula tips are placed in the central part of the nasal opening. The redirected airflow under the middle turbinate causes drying of the tissue and discomfort.

FIG. 6, element B and FIG. 7, element B show the turbulent airflow that is delivered to the nasal passage via a modified nasal prong as described herein with the bend that moves the tip of the first end closer to the lateral side of the nostril and the angled opening (compared to traditional nasal prongs). The angle of the opening protects the tissue underneath from the oxygen flow and directs the oxygen flow into the inhaled air stream restoring the normal airflow path so that the majority of airflow travels through the middle third of the nasal cavity, around the middle turbinate, about 15% travels in the lower third, and about 15% travels in the upper third. The turbulent airflow is directed superiorly and posteriorly within the nasal cavity, above the inferior concha, around the middle concha, and towards the roof or vault of the nose. The modified nasal prong can be configured to increase at least one of humidity and temperature of the airflow before the airflow reaches alveoli of the patient. Directing the turbulent airflow towards the nasal conchae can increase evaporative heat exchange between the air and mucosa (as shown in FIG. 6, element B and FIG. 7, element B) as compared to airflow from a traditional nasal prong (FIG. 6, element A and FIG. 7 element A), which increases at least one of the humidity and temperature of the airflow before it reaches the alveoli. Additionally, by directing the flow superiorly, receptors in the nasal passages that detect airflow and relieve air hunger will be stimulated.

IV. Methods

Another aspect of the present disclosure can include method 60 for improving airflow for a patient using a nasal cannula. The method 60 can be executed using the system 10 or 40 (shown in FIGS. 1-5D). For purposes of simplicity, the method 60 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 60, nor is method 60 limited to the illustrated aspects.

Figure 8:
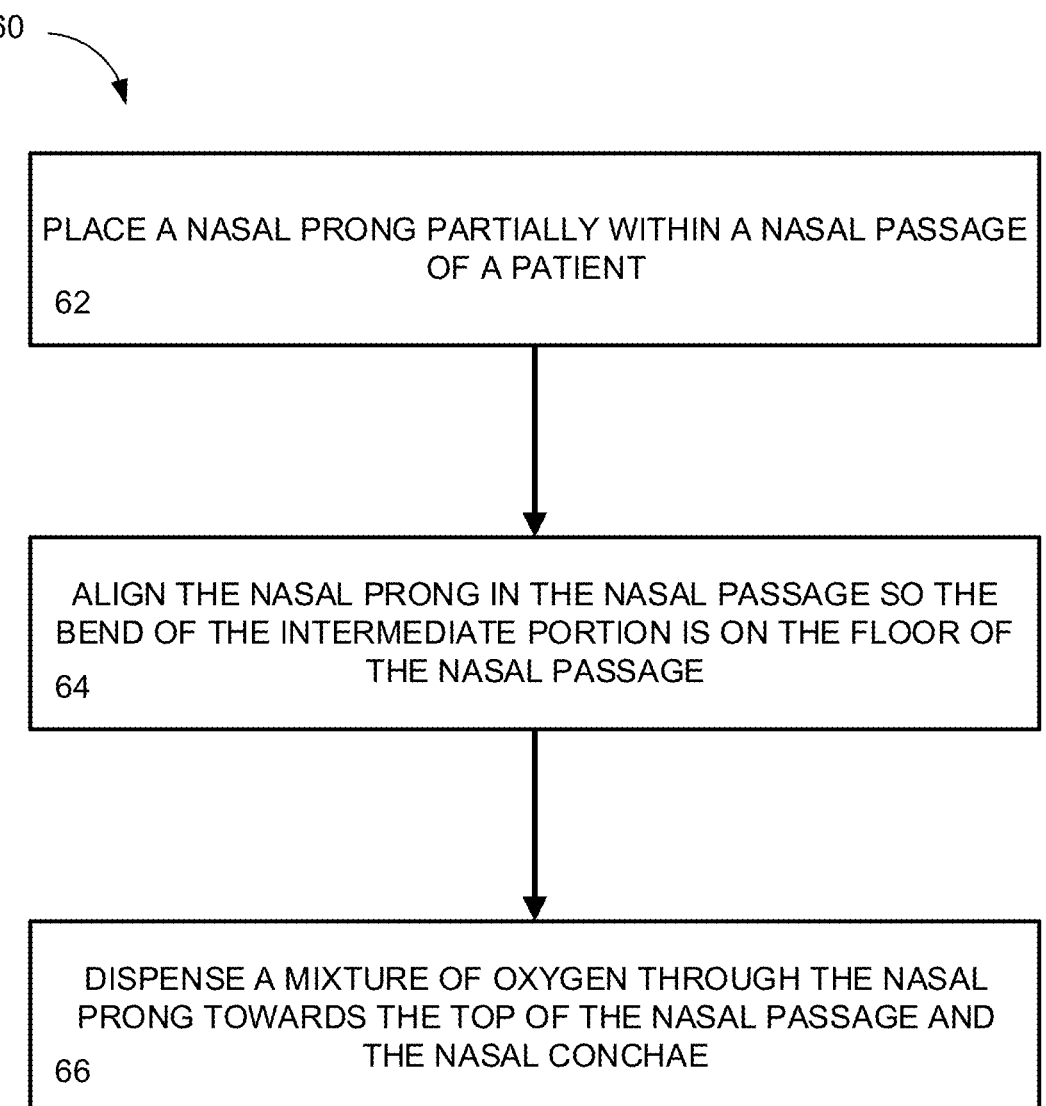
FIG. 8 is a process flow diagram illustrating a method for improving airflow to a patient.

Referring now to FIG. 8, illustrated is a method 60 for improving airflow for a patient using a nasal cannula. At 62, a nasal prong is partially placed within a nasal passage of a patient. The nasal prong is part of or attached to a nasal cannula configured for patient oxygenation (e.g., attached to an oxygenator or oxygen concentrator by medical tubing). The nasal prong can be placed in the nasal passage at least far enough to stay in place and for airflow from a first end of the nasal prong to enter the nasal passage. The nasal prong can comprise a tube configured to be partially placed in a nasal passage of a patient, the tube having a first end, a second end, and an intermediate portion, and a lumen extending therebetween. The first end having an elongated opening configured to face supero-medially when positioned within the nasal passage and the intermediate portion of the tube having a bend that keeps the nasal prong on a floor of the nasal passage. At 64, the nasal prong is aligned in the nasal passage of the patient so the bend of the intermediate portion is on the floor of the nasal passage at and/or near the outer edge of a nostril. The nasal prong can also be aligned at a depth and angle based on patient comfort level (e.g., at a comfortable alignment for the patient).

At 66, a mixture of oxygen is dispensed through the nasal prong. The mixture of oxygen is dispensed through the nasal prong in a non-laminar (e.g., turbulent) flow. The mixture of oxygen flows out of the elongated opening of the nasal prong superiorly and posteriorly within the nasal cavity, above the inferior concha, around the middle concha, and towards the roof or vault of the nose. The angle of the airflow can be between 30 and 60 degrees superior of the floor of the nasal passage. For example, the angle of the airflow can be approximately 45 degrees. Directing the airflow of the mixture of oxygen supero-medially and over at least the inferior nasal conchae is closer to the physiologic direction of airflow in the nose. By directing the flow supero-medially, the receptors within the nose that detect airflow and relieve air hunger are stimulated. The direction of the airflow also means the oxygen mixture will be better conditioned by the nasal mucosa, raising the oxygen mixtures temperature and/or humidity level to reduce crusting, dryness, nosebleed, perforation risks, and patient discomfort. When the temperature and/or humidity of the oxygen mixture is closer to physiological norms (e.g., 100% humidity and approximately 37° C.) then oxygen saturation of the patient receiving the oxygen mixture can improve due to improved alveolar gas exchange. The direction and turbulence of the airflow of the oxygen mixture can also be modified by including at least one of baffles, ridges, crimps, and rifling to an interior of the lumen of the nasal prong. The size, number, and location of the baffles, ridges, crimps, and/or rifling can change the turbulence and direction of the airflow out of the nasal prong.

From the above description, those skilled in the art will perceive improvements, changes and modifications. Such improvements, changes and modifications are within the skill of one in the art and are intended to be covered by the appended claims.

What is claimed is:

1. A nasal prong for providing airflow to a patient, the nasal prong comprising:

a tube configured to be partially placed in an entrance of a nasal passage of the patient, the tube having a first end, a second end, and an intermediate portion, and a lumen extending therebetween;

the first end configured to be positioned inside the nasal passage proximal the entrance and below a top of an inferior concha, the first end having an elongated opening to the lumen that is configured to face supero-medially within the nasal passage and towards a roof of the nasal passage to direct the airflow out of the elongated opening posteriorly and superiorly within the nasal cavity, above the inferior concha, around the middle concha, and towards the roof of the nasal passage of the patient to increase humidification and temperature of gas in the nasal passage;

the second end configured to be positioned outside the nasal passage; and the intermediate portion of the tube having a concave bend having an angle relative to a posterior portion of a nostril and that is configured to rest a portion of the bend of the nasal prong on a portion of a floor of the nasal passage at and/or near an outer posterior edge of the nostril and to face the first end supero-medially within the nasal passage.

2. The nasal prong of claim 1, wherein the second end is configured to attach to a nasal cannula.

3. The nasal prong of claim 1, wherein the second end is in fluid communication with a tubing connected to an oxygen device and a mixture of oxygen flows through the lumen into the nasal passage of the patient.

4. The nasal prong of claim 1, wherein an interior of the lumen comprises at least one of baffles, ridges, crimps, and rifling to redirect the airflow and create turbulence in the airflow.

5. The nasal prong of claim 1, wherein the elongated opening of the first end directs the airflow in a manner that also reduces at least one of an oxygen hunger, a nasal dryness, a nosebleed risk, a perforation risk, a discomfort, and a mucous crusting of the patient.

6. The nasal prong of claim 1, wherein the direction of airflow in the nasal passage is between 30 and 60 degrees superior from the floor of the nasal passage.

7. The nasal prong of claim 6, wherein the direction of airflow in the nasal passage is 45 degrees superior from the floor of the nasal passage.

8. The nasal prong of claim 1, wherein the elongated opening is elliptical or ovular in shape and angled to direct the airflow superiorly and posteriorly within the nasal passage.

9. The nasal prong of claim 8, wherein the elongated opening has a minor axis diameter of 2 mm and a major axis diameter of greater than 2 mm.

10. The nasal prong of claim 1, wherein the first end is further configured to be positioned near a portion of an outer nasal wall of the patient.

11. The nasal prong of claim 1, wherein the nasal prong is configured to make the airflow directed out of the nasal prong non-laminar to more accurately match physiological airflow through the nostril.

12. The nasal prong of claim 1, wherein the nasal prong is configured to direct the airflow in a manner that increases the humidification and temperature of the airflow before the airflow reaches at least one lung of the patient.

13. A method comprising:

placing a nasal prong partially within a nasal passage of a patient to direct airflow to the patient, wherein the nasal prong is attached to a nasal cannula and the nasal prong comprises:

a tube configured to be partially placed in the nasal passage of the patient, the tube having a first end, a second end, and an intermediate portion, and a lumen extending therebetween, the first end configured to be positioned in the nasal passage below a top of an inferior concha and having an elongated opening faced supero-medially within the nasal passage and towards a roof of the nose, the second end configured to be positioned outside the nasal passage, and the intermediate portion of the tube having a concave bend having an angle relative to a posterior portion of a nostril and that is configured to keep a portion of the bend of the nasal prong on a portion of a floor of the nasal passage at and/or near an outer posterior edge of the nostril;

aligning the nasal prong in the nasal passage of the patient so the concave bend of the intermediate portion at least partially rests on the portion of the floor of the nasal passage and the first end and the elongated opening face superior-medially within the nasal passage; and dispensing a mixture of oxygen through the nasal prong to the patient such that the elongated opening of the nasal prong directs the mixture of oxygen posteriorly and superiorly within the nasal cavity, above the inferior concha, around the middle concha, and towards the roof of the nose in a manner mimicking physiological airflow to increase humidification and temperature of the mixture of oxygen.

14. The method of claim 13, wherein the dispensing the mixture of oxygen further comprises directing the airflow out of the elongated opening of the nasal prong at an angle between 30 and 60 degrees superior of the floor of the nasal passage.

15. The method of claim 14, wherein the angle is approximately 45 degrees.

16. A nasal prong for directing airflow to a patient, the nasal prong comprising:

a tube configured to be partially placed in a front portion of a nasal passage of the patient, the tube having a first end, a second end, and an intermediate portion, and a lumen extending therebetween;

the second end comprising an opening being configured to receive laminar airflow and configured to be positioned outside the nasal passage;

a portion of the lumen being configured to alter the laminar airflow to turbulent airflow; and the first end configured to follow contours of a floor of an outer edge of an entrance of a nasal cavity and to be positioned within the nasal passage below a top of an inferior concha, wherein the first end comprises a other opening configured to direct the turbulent airflow into the nasal passage, wherein the first end is cut at an angle greater than 15° and less than 90° relative to the second end such that the other opening of the first end is elongated compared to the opening of the second end, and wherein the other opening of the first end is configured to face supero-medially in the nasal passage, towards a roof of the nose, and to direct 70% of the turbulent airflow through a middle third of the nasal cavity around a middle concha and 15% each in a lower third and an upper third of the nasal cavity, respectively, to accurately reflect a physiological airflow path and protect tissue underneath the nasal prong from a direct force of the turbulent airflow.

17. The nasal prong of claim 16, wherein the portion of the lumen is an interior of the lumen that comprises at least one of baffles, ridges, crimps, and rifling to add turbulence to the laminar airflow to create the turbulent airflow.

18. The nasal prong of claim 16, wherein the second end is configured to connect to a nasal cannula in fluid communication with an oxygen source, and the oxygen source directs laminar airflow through the nasal cannula and the nasal prong.

19. The nasal prong of claim 16, wherein the intermediate portion comprises a concave bend at an angle relative to a posterior portion of the nasal passage such that the other opening of the first end is configured to direct the turbulent airflow at least partially superiorly within the nasal passage while the concave bend at least partially holds the nasal prong in the nasal passage.

20. The nasal prong of claim 16, wherein the nasal prong is configured to reproduce physiological airflow.

* * * * *